United States Patent [19]

Ratcliffe et al.

[11] Patent Number: 5,021,565
[45] Date of Patent: Jun. 4, 1991

[54] 2-SUBSTITUTED ALKYL CARBAPENEM ANTIBACTERIALS

[75] Inventors: Ronald W. Ratcliffe, Matawan; Mary F. Woods, Metuchen, both of N.J.

[73] Assignee: Merck & Co., Inc., Rahway, N.J.

[21] Appl. No.: 541,442

[22] Filed: Jun. 21, 1990

Related U.S. Application Data

[63] Continuation of Ser. No. 396,729, Aug. 18, 1989, abandoned, which is a continuation of Ser. No. 283,016, Dec. 8, 1988, abandoned, which is a continuation of Ser. No. 163,231, Feb. 26, 1988, abandoned, which is a continuation of Ser. No. 919,725, Oct. 16, 1986, abandoned.

[51] Int. Cl.$^5$ ........................................... C07D 487/04
[52] U.S. Cl. ..................................................... 540/302
[58] Field of Search ........................................ 540/302

[56] References Cited

FOREIGN PATENT DOCUMENTS 59-104393  6/1984  Japan .

OTHER PUBLICATIONS

Chem. Abs. vol. 101, No. 25 (1984) p. 743.
J. Org. Chem., vol. 49 (1984), pp. 5271–5272.
Tetrahdron Letters, vol. 25, No. 52 (1984) pp. 5989–5992.
J. Chem. Soc. Chem. Comm., No. 22 (1984), pp. 1513–1514.

Primary Examiner—Robert Gerstl
Attorney, Agent, or Firm—John W. Harbour; Robert J. North; Hesna J. Pfeiffer

[57] ABSTRACT

Described is a new process for producing new 2-substituted alkyl-3-carboxycarbapenems, involving condensation of a 2-oxocarbapenam-3-carboxylic ester with a stabilized ylide followed by ester deblocking. The resulting carbapenem compounds, which are not readily available from other known synthetic routes, show interesting antibacterial activity.

9 Claims, No Drawings

2-SUBSTITUTED ALKYL CARBAPENEM ANTIBACTERIALS

This is a continuation, of U.S. application Ser. No. 396,729, filed 8/18/89 now abandoned which is a continuation of application Ser. No. 283,016, filed Dec. 8, 1988 now abandoned which is a continuation of U.S. application Ser. No. 163,231, filed Feb. 26, 1988 now abandoned which is a continuation of U.S. application Ser. No. 919,725, filed Oct. 16, 1986 now abandoned.

BACKGROUND OF THE INVENTION

1. Field of the Invention

This invention relates to novel 2-substituted alkyl-3-carboxycarbapenem antibacterials obtained from condensation of a 2-oxocarbapenam-3-carboxylic ester with a stabilized ylide followed by removal of the ester protecting group.

2. Brief Discussion of Disclosures in the Art

2-Substituted alkyl carbapenems are known in the art as exhibiting interesting antibacterial activity. For example, see U.S. Pat. Nos. 4,539,208 and 4,194,047, both assigned to Merck & Co. Inc.

The process generally used for producing these compounds is multistep one whose crucial ring-forming reaction generally involves an internal Wittig reaction as illustrated by the following synthetic scheme:

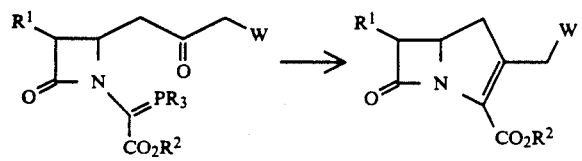

However the overall synthesis is a lengthy one, and does not work efficiently for certain W groups, e.g., COR, CO$_2$R and CN.

Sandoz has recently reported in *Tetrahedron Letters*, Vol. 25, No. 52, pp. 5989–5992 (1984) the Wittig reaction between 6-fluoroalkyl 2-oxocarbapenam-3-carboxylic esters ketoesters and triphenylphosphorane ylides. However, it is disclosed that difficulties were found in attempting to remove the 3-(para-nitrobenzyl carboxylate) protecting group and that carbapenams and inseparable mixtures were obtained. It is further stated that none of the obtained compounds exhibited interesting antibacterial activity.

3. Objects of the Invention

It is an object of the present invention to provide an improved process for synthesizing 2-substituted alkyl-3-carboxycarbapenems in a rapid and convenient route starting with a readily available 2-oxocarbapenam-3-carboxylic ester. It is further an object to provide a process yielding novel 2-substituted alkyl-3-carboxycarbapenems separated from their relatively inactive 2-substituted alkylidene-3-carboxycarbapenam by-products. These and other objects of the invention will be obvious to one skilled in the art from the following disclosure.

SUMMARY OF THE INVENTION

In accordance with this invention there is provided a process comprising the step of contacting a compound of the structural formula:

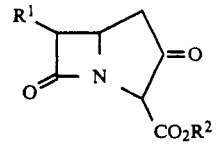

wherein $R^1$ is independently selected from H, $C_1$-$C_3$ linear or branched alkyl optionally substituted with hydroxy or protected hydroxy; $R^2$ is an ester protecting group; with a phosphorane of the structural formula:

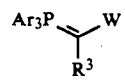

wherein W is independently selected from CN, COR$^4$, or CO$_2$R$^4$, wherein R$^3$ is selected from hydrogen or $C_1$-$C_4$ alkyl, and R$^4$ is selected from $C_1$-$C_4$ alkyl $C_7$-$C_{11}$ aralkyl, wherein the aryl portion and Ar are phenyl or phenyl substituted with chloro, $C_1$-$C_3$ alkoxy, or di($C_1$-$C_3$ alkyl)amino, in an inert solvent, in the temperature range of −10° to 40° C., to form a compound of the structural formula:

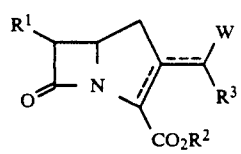

wherein the dotted line represents either an endo or exo double bond, or mixture thereof.

The exo isomers of structure III can exist or either the E or Z forms or as mixtures of the two. These structures are shown below in addition to the endo isomer:

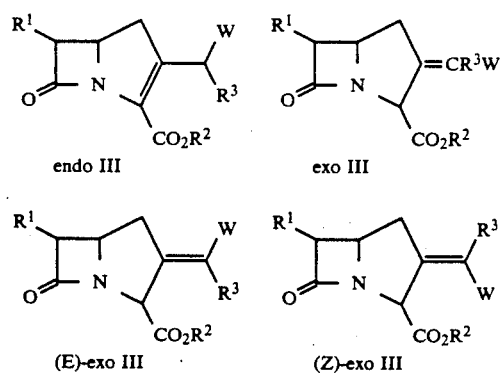

endo III     exo III (E)-exo III     (Z)-exo III

Removal of the ester blocking group of III results in a compound of the structural formulae:

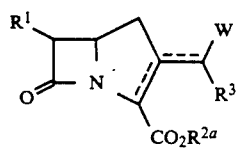

wherein $R^{2a}$ is H or a water soluble cation and IV encompasses the endo and exo forms shown below:

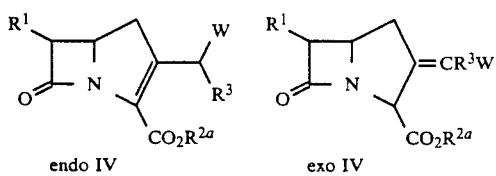
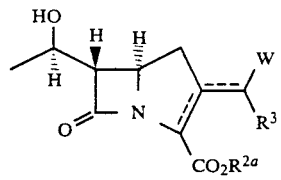

endo IV     exo IV

Also provided is a process comprising the steps of (a) contacting a compound of the structural formula:

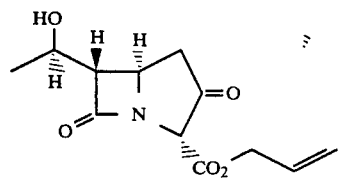

I with a phosphorane of the structural formula:

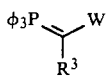

II wherein W and $R^3$ are as previously defined in an inert solvent, in the temperature range of about 0° C. to 25° C., to form a compound of the structural formula:

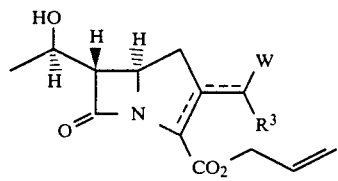

V wherein the dotted line represents either an endo or exo double bond, or mixture thereof; or shown by the structures below:

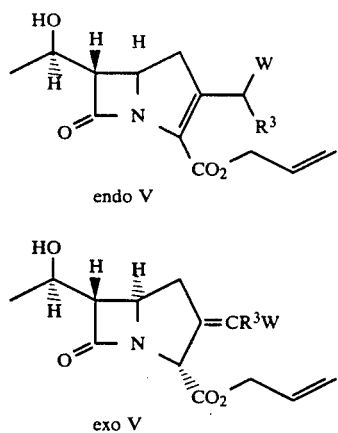

endo V exo V (b) removing the ester allyl group by contacting with a mixture of a Pd°-phosphine complex, a branched chain alkanoic acid or potassium salt, and an inert solvent therefor, resulting in a compound of the structural formula:

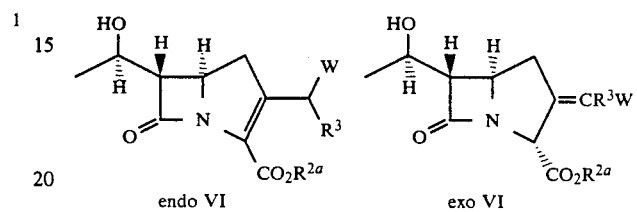

VI wherein $R^{2a}$ is H or a water-soluble cation. Structure VI encompasses both the following endo and exo forms:

endo VI     exo VI

Further provided is a compound of the structural formula:

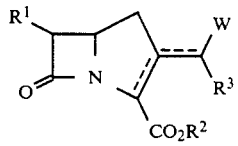

wherein $R^1$ is independently selected from $C_1-C_3$ linear or branched alkyl optionally substituted with hydroxy or protected hydroxy; $R^{2a}$ is an ester protecting group, H or a water-soluble cation; W is selected from CN or $CO_2R^4$, wherein $R^3$ is selected H or $C_1-C_4$ alkyl, and $R^4$ is selected from $C_1-C_4$ alkyl, $C_7-C_{11}$ aralkyl, and wherein the dotted line represents an endo or exo double bond, or mixture thereof, with the proviso that when W is CN, the double bond is exo.

DESCRIPTION OF INVENTION AND PREFERRED EMBODIMENTS

The overall process of the instant invention can be depicted from the following synthetic scheme:

Step (1)

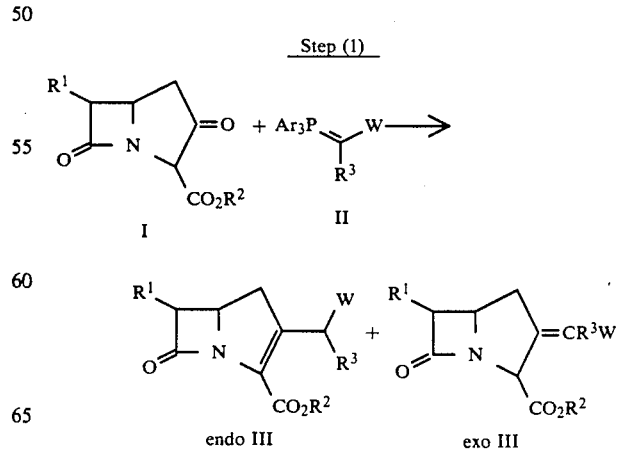

endo III     exo III

Step (2)

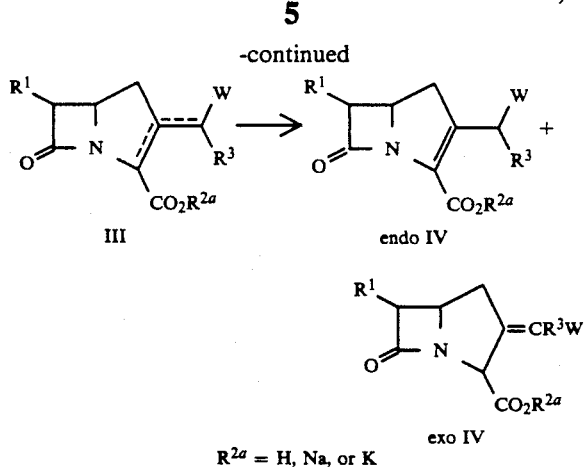

$R^{2a}$ = H, Na, or K

The bicyclic ketoester starting material I is readily available where $R^1$ is H, $C_1$-$C_4$ alkyl, hydroxy substituted $C_1$-$C_4$ alkyl, or protected hydroxy $C_1$-$C_4$ alkyl. References describing its synthesis are: U.S. Pat. Nos. 4,369,187 and 4,318,912, both assigned to Merck & Co. Inc., hereby incorporated by reference for this purpose.

The triarylphosphorane ylide is also readily available and can be made by synthesis described in the references: A. W. Johnson, *Ylide Chemistry*, Academic Press, N.Y. (1966); A. Maercker, *Organic Reactions*. Vol. 14, 270–490 (1965), hereby incorporated by reference for this particular Purpose.

In Step (1) the Wittig condensation is carried out in an inert dry solvent. Representative examples of inert solvents are chloroform, methylenechloride, tetrahydrofuran and dioxane. A preferred solvent for use in the initial step is methylene chloride.

The temperature that the Wittig reaction is carried out is in the range of −10° to 40° and preferably in the range of 0° to 25° C.

The reaction is carried out under a pressure of 1 atmosphere and preferably under an inert atmosphere of nitrogen or argon.

Concentration of the phosphorus ylide and bicyclic ketoester under the conditions in the solvent is normally in the range of about 0.05 to 0.5 molar and preferably 0.2–0.3 molar. Generally, one to two equivalents of the ylide reagent are used per equivalent of bicyclic ketoester and preferably 1.5 equivalents.

Time for the reaction is generally in the range of 0.5–10 hours and preferably 1–3 hours.

Structure III, the Wittig product, can be isolated by conventional techniques in the art including filtration, washing, centrifugation, chromatography and the like. Yields of structure III from the Wittig reaction are in the range of 10 to 100% and preferably 70–90%. These materials are then used in Step (2), ester blocking group removal, e.g. by catalytic hydrogenation, ester exchange and the like, to derive the free acids which display antibacterial activity.

When $R^2$ is benzyl, para-nitrobenzyl (PNB), catalytic hydrogenation can be used for the ester group removal. For example, conventional palladium on carbon catalyst suspension in tetrahydrofuran, dioxane, ethanol, water, or mixtures thereof, optionally in the presence of a base such as sodium bicarbonate or potassium bicarbonate solvent, at room temperature and 1-3 atmospheres hydrogen pressure, for 1-3 hours will produce isolated mixtures of exo and endo forms. The yields of endoIV obtained by this process are generally low and unacceptable. The major products produced by hydrogenolytic deblocking are the fully saturated, overreduction carbapenam products shown below:

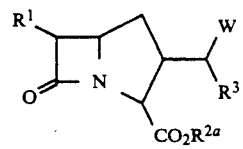

A preferred method of removing the protecting group is when $R^2$ is allyl and the allyl group is exchanged with hydrogen, sodium, or potassium by contacting with a mixture containing an alkanoic acid or an alkali alkanoate, preferably 2-ethylhexanoic acid, sodium 2-ethylhexanoate, or potassium 2-ethylhexanoate, and a palladium (O) complex, preferably tetrakis(triphenyl phosphine)palladium, in ethylacetate, methylene chloride, tetrahydrofuran or mixtures thereof, at 0°–25° C., under an inert atmosphere(nitrogen or argon) for 0.2–0.5 hours to produce IV.

The yields of obtained IV are in the range of 10 to 60%. By the reaction described herein mixtures of exo and endo isomers, i.e. depicted above, are obtained, generally in a ratio of 1:3 to 1:1. The endo isomer being the more desirable is favored in the process when W is strongly electron withdrawing e.g. $COR^4$, $CO_2R^4$ and the ratio then obtained is endo:exo of 3:1. The endo and exo products can conveniently be separated by the techniques of chromatography and/or fractional crystallization.

Analytically the presence of the exo and endo isomers in a crude reaction mixture is seen in the IR, UV, and NMR spectra and can be spectrally differentiated on this basis.

Yields of the desired endo product overall from the process range from 15 to 60%.

Conventional apparatus can be used in the art for carrying out the subject process described herein.

Also a subject of this invention are the novel compounds of the structure as described above in the Summary of the Invention and prepared by the processes described above. In the formula, $R^1$ is independently selected from hydrogen, $C_1$-$C_3$ linear or branched alkyl optionally substituted with hydroxy or protected hydroxy. Representative examples are ethyl, 1-hydroxyethyl, $(CH_3)_2C(OH)$-, 1-(t-butyldimethyl)siloxyethyl, and 1-(allyloxycarbonyloxy)ethyl. Preferred is where $R^1$ is 1-hydroxyethyl in the R configuration and the configuration of the carbapenem nucleus in 5R,6S.

$R^2$ is a readily removable ester protecting group. Representative examples include benzyl, para-nitrobenzyl, allyl, and 2-chloroallyl. A preferred ester protecting group is allyl.

$R^3$ is selected from hydrogen or $C_1$-$C_4$ alkyl. Preferred is where $R^3$ is hydrogen.

W is independently selected from CN, $COR^4$, or $CO_2R^4$ where $R^4$ is selected from $C_1$-$C_4$ alkyl, $C_7$-$C_{11}$ aralkyl. Preferred is where $R^4$ is methyl. A preferred W is where W is $CO_2Me$ or CN. $R^{2a}$ is hydrogen or a water soluble cation selected from sodium, potassium, ammonium and the like. Preferably $R^{2a}$ is sodium or potassium. The following compounds are particularly preferred within the formula described above as follows:

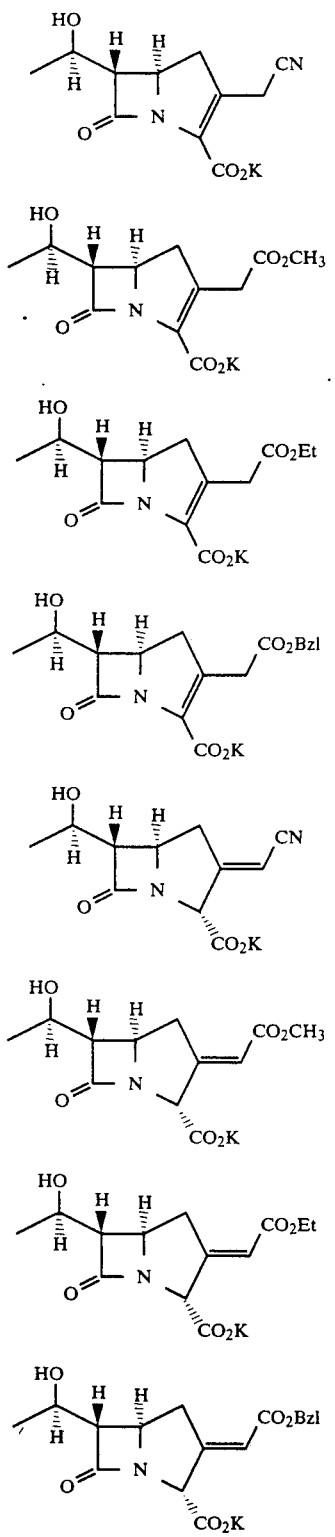

The novel compounds in the different chemical classes of the present disclosure are believed to be valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella oneumoniae. Bacillus subtilis. Salmonella typhosa Psuedomonas* and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat Paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day.

A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described herein, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above, schematic reaction diagram for the total synthesis of the defined antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

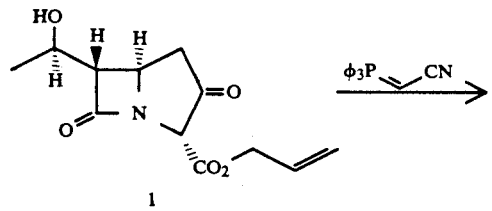

1

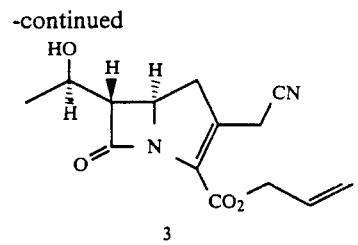

3

Allyl (5R,6S)-2-[(E)-cyanomethylene]-6-[1(R)-hydroxyethyl]carbapenam-3(R)-carboxylate (2) and allyl (5R,6S)-2-cyanomethyl-6-[1(R)-hydroxyethyl]carbapen-2-em-3-carboxylate (3)

A solution of allyl (5R,6S)-6-[1(R)-hydroxyethyl]-2-oxo-carbapenam-3(R)-carboxylate (1) (50.7 mg, 0.2 mmol) and (cyanomethylene)triphenylphosphorane (90.5 mg, 0.3 mmol) in anhydrous chloroform-d (1.0 ml) was kept at room temperature under a nitrogen atmosphere for 4 hours. The resulting mixture was chromatographed on a column of EM silica gel 60 (20 g) using 1:1 ethyl acetate-methylene chloride as eluting solvent; 15 ml fractions were collected every 1.5 minutes. Fractions 4–7 were combined and evaporated under vacuum to afford a 55:45 mixture of 2 and 3 (41.9 mg, 76% yield) as a clear oil.

Compound 2: NMR (CDCl$_3$)δ 1.36 (d, J=6.4 Hz, CH$_3$CHOH), 2.79 (dddd, J=1.0, 3.2, 6.7 and 19.0 Hz, H1a), 3.09 (dd, J=2.0 and 7.0 Hz, H6), 3.36 (dddd, J=2.0, 2.0, 7.1 and 19.0 Hz, H1b), 4.15 (dt, J=2.0 and 7.0 Hz, H5), 4.27 (m, CH$_3$CHOH), 5.11 (ddd, J=1.0, 2.0 and 2.2 Hz, H3), 5.67 (ddd, J=2.0, 1 2.2 and 3.2 Hz, CHCN).

Compound 3: NMR (CDCl$_3$)δ 1.35 (d, J=6.4 Hz, CH$_3$CHOH), 3.02 (ddt, J=8.8, 18.8 and 1.5 Hz, H1a), 3.16 (ddt, J=9.7, 18.8 and 1.5 Hz, H1b), 3.24 (dd, J=2.9 and 6.5 Hz, H6), 3.75 and 3.95 (two dt, J=18.9 and 1.5 Hz, CH$_2$CN), 4.27 (m, H5 and CH$_3$CHOH).

IR (film) 2230, 1755 (br) cm$^{-1}$.

Mass spectrum m/e 276 (M$^+$), 232, 190.

EXAMPLE 2

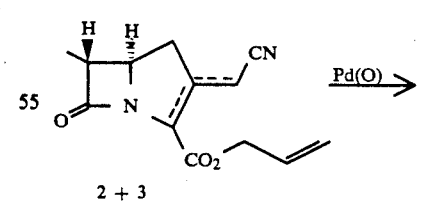

2 + 3

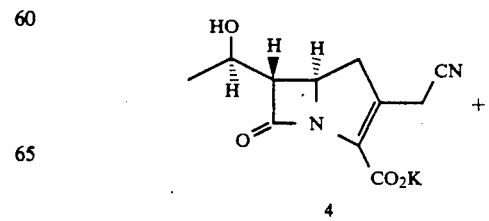

4

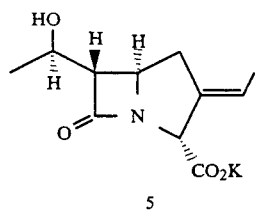

Potassium
(5R,6S)-2-cyanomethyl-6-[1(R)-hydroxyethyl]-carbapen-2-em-3-carboxylate (4) and potassium
(5R,6S)-2-[(E)-cyanomethylene]-6-[1(R)-hydroxyethyl]-carbapenam-3-(R)-carboxylate (5)

A solution of isomers 2 and 3 (19.9 mg, 0.072 mmol) and triphenylphosphine (5.7 mg, 0.022 mmol) in anhydrous methylene chloride (1.4 ml) was treated with 2-ethylhexanoic acid (34.5 μl, 0.216 mmol) and tetrakis(triphenylphosphine)palladium (6.6 mg, 0.0057 mmol). The solution was stirred at room temperature and under a nitrogen atmosphere for 10 minutes, then treated with 0.5M potassium 2-ethylhexanoate in ethyl acetate (144 μl, 0.072 mmol). After stirring two minutes, the solution was diluted with ethyl ether to give a pale yellow precipitate that was collected by centrifugation and washed with ethyl ether (3x). The precipitate was dissolved in water (10 ml), filtered through a Gelman 0.45 μm CR acrodisc and lyophilized to provide the crude product mixture (ca. a 2:3 ratio of 4:5 by NMR) as a pale yellow solid (21 mg).

The crude product was chromatographed on an Analtech 0.5 mm×20×20 cm RPS-F plate using 5% ethanol in water as the developing solvent in a cold room. Two major UV visible bands were removed and each was eluted with 4:1 acetonitrile-water, diluted with water, extracted with petroleum ether, concentrated under vacuum to ca. 5 ml, filtered through a CR acrodisc, and lyophilized.

The band centered at $R_f$ 0.71 gave the endocyclic isomer 4, contaminated with ca. 20% of the exocyclic isomer, as a white, amorphous solid (2.6 mg, 13%): NMR (D$_2$O) δ 1.09 (d, J=6.4 Hz, CH$_3$CH), 2.85 (d, J=9.2 Hz, CH$_2$), 3.23 (dd, J=2.8 and 6.0 Hz, H6), 3.58 and 3.74 (two d's, J=18.2 Hz, CH$_2$CN), 4.03 (m, H5 and CH$_3$CH), 4.61 (HOD); IR (Nujol) 3380 (br), 2230, 1755, 1600 cm$^{-1}$; UV (0.05 M pH 7.0 MOPS buffer) $\lambda_{max}$ 265 nm (E$^{1\%}$ 95); UV (buffer+NH$_2$OH.HCl) $\lambda_{max}$ ext. 268 nm (E$^{1\%}$ ext. 86).

The band centered at $R_f$ 0.82 gave the exocyclic isomer 5, contaminated with ca. 5% of the endocyclic isomer, as a white, amorphous solid (7.2 mg, 37%): NMR (D$_2$O) δ 1.11 (d, J=6.5 Hz, CH$_3$CH), 2.70 (ddd, J=2.6, 7.0 and 18.8 Hz, H1a), 3.09 (dd, J=1.8 and 6.2 Hz, H6), 3.12 (tdd, J=1.7, 7.0 and 18.8 Hz, H1b), 3.90 (dt, J=1.8 and 7.0 Hz, H5), 4.07 (dq, J=6.4 Hz, CH$_3$CH), 4.61 (HOD), 4..80 (m, H3), 5.61 (m, CHCN); IR (Nujol) 3390 (br), 2230, 1755, 1620 cm$^{-1}$; UV (0.05M pH 7.0 MOPS buffer) $\lambda_{max}$ 223 nm (E$^{1\%}$ 350)

EXAMPLE 3

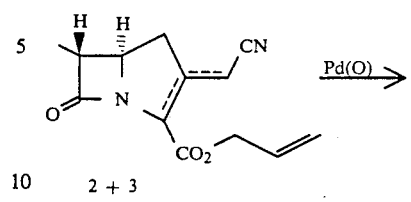

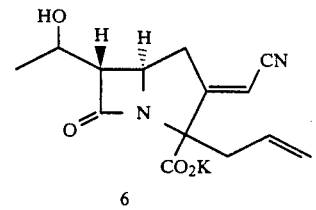

Potassium
(5R,6S)-3-allyl-2-[(E)-cyanomethylene]-6-[1(R)-hydroxyethyl]carbapenam-3-carboxylate (6)

A solution of the cyano mixture (36.5 mg, 0.132 mmol) and triphenylphosphine (10.4 mg, 0.04 mmol) in 1:1 ethyl acetate-methylene chloride (2.4 ml) was treated with 0.5M potassium 2-ethylhexanoate in ethyl acetate (264 μl, 0.132 mmol) and tetrakis(triphenylphosphine)palladium (12.2 mq, 0.01 mmol). The resulting mixture was stirred at room temperature under a nitrogen atmosphere for 15 minutes, then diluted with diethyl ether (20 ml) and centrifuged. The solid pellet was washed with ether and dried under vacuum to an off-white solid. The NMR spectrum of this material showed little, if any, of the desired products and mainly the C3 alkylated product.

The crude product was chromatographed on two Analtech 0.5 mm×20×20 cm RPS-F plates which were developed with 10% ethanol in water in a cold room. The major UV visible band centered at $R_f$ 0.75 was eluted with 4:1 acetonitrile-water (4×). The eluant was diluted with water, washed with petroleum ether (2×), concentrated under vacuum to ca. 15 ml, filtered through a Gelman 0.45 μm CR acrodisc, and lyophilized to give the title compound (11.5 mg, 28%) as an off-white, amorphous solid: NMR (D20) δ 1.30 (d, J=6.4 Hz, CH$_3$CH), 2.9 (m and H1a), 3.23 (dd, J=1.7 and 6.4 Hz, H6), 25 (ddd, J=2.1, 7.0 and 18.4 Hz, H1b), 3.97 (dt, J=1.7 and 7.0 Hz, H5), 4.25 (dq, J=6.4 Hz, CH$_3$CH), 5.22 (m, CH═CH$_2$), 5.74 (dd, J=1.7 and 2.9 Hz, ═CHCN), 5.89 (m, CH═CH$_2$) and 4.80 (HOD); IR (Nujol) 3370 (br), 2215, 1735, 1615 cm$^{-1}$; UV (H$_2$O) $\lambda_{max}$ 225 (sh) nm.

EXAMPLE 4

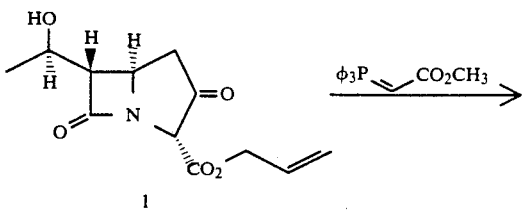

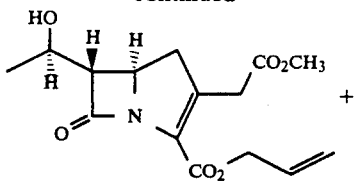

7

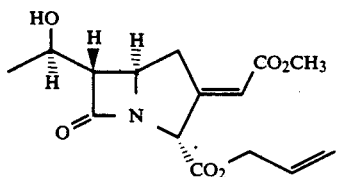

8

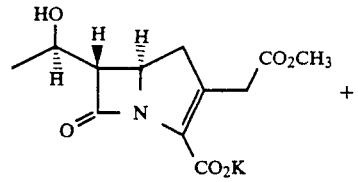

10

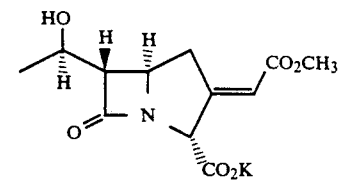

11

Allyl (5R,6S)-2-carbomethoxymethyl-6-[1(R)-hydroxyethyl]carbapen-2-em-3-carboxylate (7) and allyl (5R,6S)-2-[(E)-carbomethoxymethylene]-6-[1(R)-hydroxyethyl]carbapenam-3(R)-carboxylate (8)

A solution of the bicyclic ketoester 1 (50.7 mg, 0.2 mmol) and (carbomethoxymethylene)triphenylphosphorane (100.3 mg, 0.3 mmol) in anhydrous methylene chloride (2.0 ml) was stirred at room temperature under a nitrogen atmosphere for 3 hours. The reaction mixture was added to a column of EM silica gel 60 (10 g) which was eluted with 1:1 ethylacetate-methylene chloride at a rate of 15 ml fractions every 3.5 minutes. Fractions 3-9 gave a 3:1 mixture of products 7 and 8 and triphenylphosphine oxide as a clear oil (88 mg).

Compound 7: NMR (CDCl$_3$) δ 1.35 (d, J=6.4 Hz, CH$_3$CH), 2.99 (br d, J=9 Hz, H1aH1b), 3.20 (dd, J=2.8 and 7.0 Hz, H6), 3.67, 3.83 (two br d's, J=17 Hz, CH$_2$CO$_2$CH$_3$), 3.71 (s, CO$_2$CH$_3$), 4.23 (m, H5 and CH$_3$CH), 4.75 (m CH$_2$CH=CH$_2$) 5.39 (m, CH$_2$CH=CH$_2$), 5.92 (m, CH$_2$CH=CH$_2$).

Compound 8: NMR (CDCl$_3$) δ 1.36 (d, J=6.4 Hz CH$_3$CH), 2.95 (m, H1aH1b), 3.05 (dd, J=2.0 and 6.9 Hz, 3.74 (s, CO$_2$CH$_3$), 4.13 (dt, J=2.0 and 7.0 Hz, H5), 4.26 (m, CH$_3$CH), 4.65 (m, CH$_2$CH=CH$_2$), 5.10 (br s, H3), 5.39 (m, CH$_2$CH=CH$_2$), 5.90 (m, CH$_2$CH=CH$_2$), 6.11 (m, =CHCO$_2$CH$_3$).

EXAMPLE 5

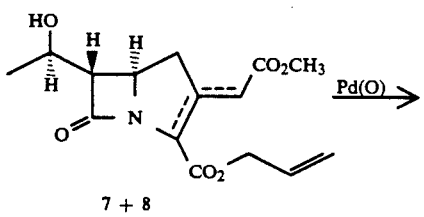

7 + 8

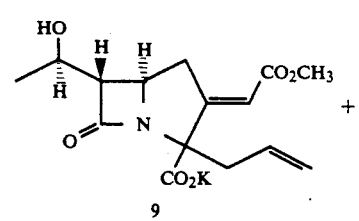

9

Potassium (5R,6S)-3-allyl-2-[(E)-carbomethoxymethylene-6-[1(R)-hydroxyethyl]carbapenam-3-carboxylate (9), potassium (5R,6S)-2-carbomethoxymethyl-6-[1(R)-hydroxyethyl]carbapen-2-em-3-carboxylate (10) and potassium (5R,6S)-2-[(E)-carbomethoxymethylene]-6-[1(R)-hydroxyethyl]carbapenam-3(R)-carboxylate (11)

A solution of the crude product mixture from the preceding example and triphenylphosphine (15.7 mg, 0.06 mmol) in 1:1 ethylacetate-methylene chloride (3.6 ml) was treated with 0.5M potassium 2-ethylhexanoate in ethylacetate (0.40 ml, 0.2 mmol) and with tetrakis(triphenylphosphine)palladium (18.5 mg, 0.016 mmol). The mixture was stirred at room temperature under a nitrogen atmosphere for 15 minutes, then diluted with ethyl ether (20 ml) and centrifuged. The solid portion was washed with ether (2×10 ml), taken up in a small volume of water, and streaked on two Analtech 0.5 mm×20×20 cm RPS-F plates that were developed in a cold room using 10% ethanol in water. Four UV visible bands were removed and each was eluted with 4:1 acetonitrile-water. Each eluant was diluted with water, washed with petroleum ether, filtered through a Gelman 0.45 μm CR acrodisc, concentrated under vacuum to ca. 5 ml, and lyophilized.

The band centered at R$_f$ 0.55 gave an amorphous solid (5.3 mg) tentatively identified by UV and NMR spectroscopy as a mixture of 2'-allylated structures related to carbapenem 10.

The band centered at R$_f$ 0.61 gave the 3-allylated carbapenam 9 as an amorphous solid (5.2 mg) NMR (D$_2$O) δ 1.31 (d, J=6.5 Hz, CH$_3$CH), 2.9 (m, H1a and CH$_2$CH=CH$_2$), 3.17 (dd, J=1.5 and 6.5 Hz, H6), 3.44 (ddd, J=2.0, 7.0 and 19.5 Hz, H1b), 3.76 (s, CO$_2$CH$_3$), 3.94 (dt, J=1.5 and 7.0 Hz, H5), 4.25 (dq, J=6.5 Hz, CH$_3$CH), 4.84 (HOD), 5.2 (m, CH=CH$_2$), 4.9 (m, CH=CH$_2$), 6.10 (dd, J=2.0 and 2.5 Hz, =CHCO$_2$CH$_3$).

The band centered at Rf 0.68 provided the carbapenem 10 (18.3 mg) as an amorphous solid: NMR (D$_2$O) δ 1.22 (d, J=6.4 Hz, CH$_3$CH), 2.88 (m, H1aH1b), 3.34 (dd, J=2.8 and 6.0 Hz, H6), 3.50 and 3.74 (two d's, J=16.5 Hz, CH$_2$CO$_2$CH$_3$), 3.66 (s, CO$_2$CH$_3$), 4.13 (dt, J=2.8 and 8.8 Hz, H5), 4.18 (dq, J=6.3 Hz, CH$_3$CH), 4.78 (HOD); IR (Nujol) 3370 (br), 1730 (br), 1590 (br) cm$^{-1}$; UV (H$_2$O) λ$_{max}$ 268 nm (E$^{1\%}$ 90, 89% NH$_2$OH extinguished).

The band centered at $R_f$ 0.74 provided the carbapenam 11 (7.7 mg) as an amorphous solid: NMR (D$_2$O) δ 1.26 (d, J=6.4 Hz, CH$_3$CH), 2.85 (ddd, J=2.5, 6.5 and 19.5 Hz, H1a), 3.20 (dd, J=1.7, 6.3 Hz, H6), 3.49 (tdd, J=1.7, 7.3 and 19.5 Hz, H1b), 3.70 (s, CO$_2$CH$_3$), 4.05 (dt, J=1.7 and 7.0 Hz, H5), 4.23 (dq, J=6.4 Hz, CH$_3$CH), 4.79 (HOD), 4.91 (m, H3), 6.14 (m, =IR (Nujol) 3380 (br), 1735, 1710, 1605 cm$^{-1}$; UV (H$_2$O) $\lambda_{max}$ 220 nm.

EXAMPLE 6

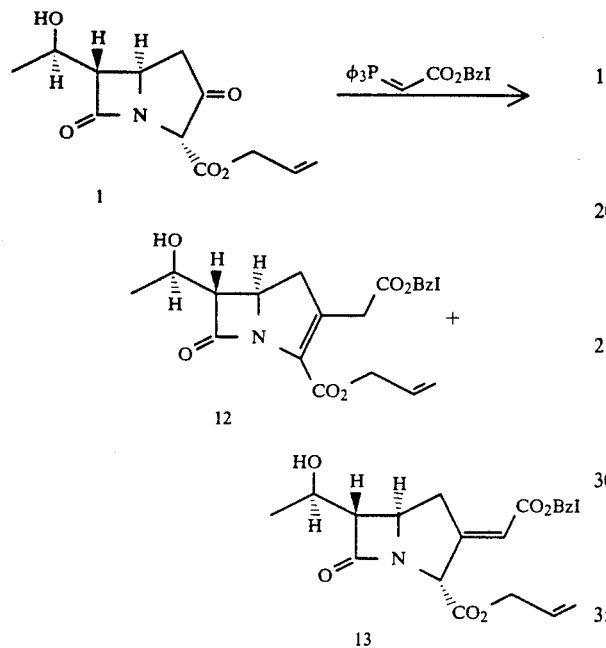

Allyl (5R,6S)-2-carbobenzyloxymethyl-6-[1(R)-hydroxyethel]carbapen-2-em-3-carboxylate (12) and allyl (5R,6S)-2-[(E)-carbobenzyloxymethylene]-6-[1(R)-hydroxyethyl]carbapenam-3(R)-carboxylate (13)

A solution of the bicyclic keto ester 1 (50.7 mg, 0.2 mmol) and (carbobenzyloxymethylene)triphenylphosphorane (123.2 mg, 0.3 mmol) in anhydrous chloroform-d (1.0 ml) was stirred under a nitrogen atmosphere at room temperature. Aliquots (25 µl) were removed periodically, added to chloroform-d (0.5 ml), and examined by NMR spectroscopy to assess the progress of the reaction. After 3.25 hours, the reaction mixture was added to a column of EM silica gel 60 (10 g) which was eluted with 1:1 ethylacetatemethylene chloride at a rate of 8 ml fractions every 2 minutes. Fractions 4–6 were combined to give a 3:1 mixture of products 12 and 13 as a clear oil (59 mg, 77%).

Addition of a small amount of diethyl ether to the product mixture resulted in crystallization of compound 12. The crystals were washed with ether and dried under vacuum to give the endocyclic isomer 12 (35 mg) as fine, white needles: m.p. 94°-96° (micro hot stage); NMR (CDCl$_3$) δ 1.34 (d, J=6.4 Hz, CH$_3$CH), 1.63 (d, J=5.0 Hz, OH), 2.95 (m, H1aH1b), 3.14 (dd, J=2.9 and 6.7 Hz, H6), 3.68 and 3.86 (two d's, J=16.6 Hz, CH$_2$CO$_2$Bzl), 4.18 (dt, J=2.9 and 9.2 Hz, H5), 4.23 (m, CH$_3$CH), 4.74 (m, CH$_2$CH=CH$_2$), 5.15 (s, CH$_2$C$_6$H$_5$), 5.35 (m, CH=CH$_2$), 5.94 (m, CH=CH$_2$), 7.38 (s, C$_6$H$_6$); IR (CH$_2$Cl$_2$) 3580, 1772, 1730, 1715 cm$^{-1}$; UV (dioxane) $\lambda_{max}$ 282 nm (ε6020); mass spectrum m/e 385 (M$^+$), 300.

The exocyclic isomer 13 exhibited the following characteristic NMR resonances: NMR (CDCl$_3$) δ 1.36 (d, J=6.3 Hz CH$_3$CH), 2.90 (m, H1a), 3.05 (dd, J=2.0 and 7.0 Hz, H6), 3.59 (tdd, J=2.4, 7.4 and 20.3 Hz, H1b), 5.10 (m, H3), 5.18 (s, CH$_2$C$_6$H$_5$), 6.16 (m, =CHCO$_2$).

EXAMPLE 7

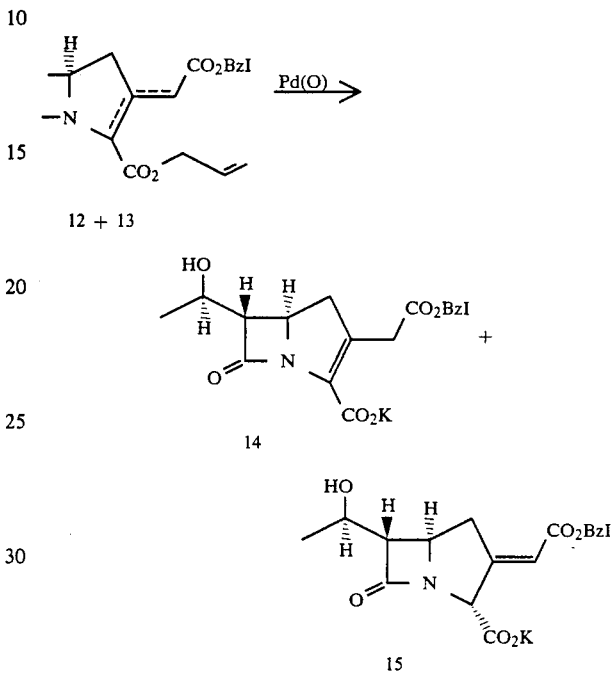

Potassium (5R,6S)-2-carbobenzyloxymethyl-6-[1(R)-hydroxyethyl]carbapen-2-em-3-carboxylate (14) and potassium (5R,6S)-2-[(E)-carbobenzyloxymethylene]-6-[1(R)-hydroxyethyl]carbapenam-3(R)-carboxylate (15)

A 3:1 mixture of isomers 12 and 13 (33 mg, 0.0856 mmol) and triphenylphosphine (6.7 mg, 0.0255 mmol) were dissolved in 1:1 ethyl acetate-methylene chloride (1.54 ml). The solution was treated with 0.5M potassium 2-ethylhexanoate in ethyl acetate (171 µl, 0.0856 mmol) and tetrakis(triphenylphosphine)palladium (8.2 mg, 0.0071 mmol), then stirred at room temperature under a nitrogen atmosphere for 15 minutes. The mixture was diluted with diethyl ether (10 ml) and centrifuged. The solid residue was washed with ether (2×5 ml), taken up in water (1 ml), and streaked on two Anatech 0.25 mm×20×20 cm RPS-F plates. The plates were developed in a cold room with 15% ethanol in water. The major UV visible band was removed, eluted with 4:1 acetonitrile-water (4×5 ml), diluted with water (20 ml), washed with petroleum ether (2×20 ml), concentrated under vacuum to ca. 5 ml volume, and lyophilized to provide a 55:45 mixture of products 14 and 15 as a white, amorphous powder (10.8 mg): IR (Nujol) 3330 (br), 1740 (br), 1600 (br) cm$^{-1}$; UV (0.05M pH 7.0 MOPS buffer) $\lambda_{max}$ 269 nm (sh, 74, 78% extinguished with NH$_2$0H).

The NMR spectrum of the mixture was analyzed as follows Compound 14 NMR (D$_2$O) δ 1.26 (d, J=6.4, CH$_3$CH), 2.85 (d, J=9.2 Hz, H1aH1b), 3.27 (dd, J=2.7 and 6.1 Hz, H6), 3.63 and 3.78 (two d's, J=16.6 hz, CH$_2$CO$_2$), 4.13 (dt, J=2.8 and 9.2 Hz, H5), 4.20 (dq, J=6.4 Hz, CH₃CH), 4.82 (HOD), 5.19 (s, CO₂CH₂), 7.47 (s,C₆H₅); Compound 15 NMR (D₂O) δ 1.30 (d, J=6.4 Hz, CH₃CH), 2.87 (m, H1a), 3.21 (dd, J=1.8 and 6.3 Hz, H6), 3.52 (m, H1b), 4.07 (dt, J=1.8 and 7.0 Hz, H5), 4.26 (dq, J=6.4 Hz, CH₃CH), 4.82 (HOD), 4.94 (m, H3), 5.23 (s, CO₂CH₂), 6.21 (m, =CHCO₂), 7.47 (s, C₆H₅).

The crude product before reverse phase chromatography also showed NMR resonances consistent with a minor amount of a C3-allylated carbapenam related to compound 9.

EXAMPLE 8

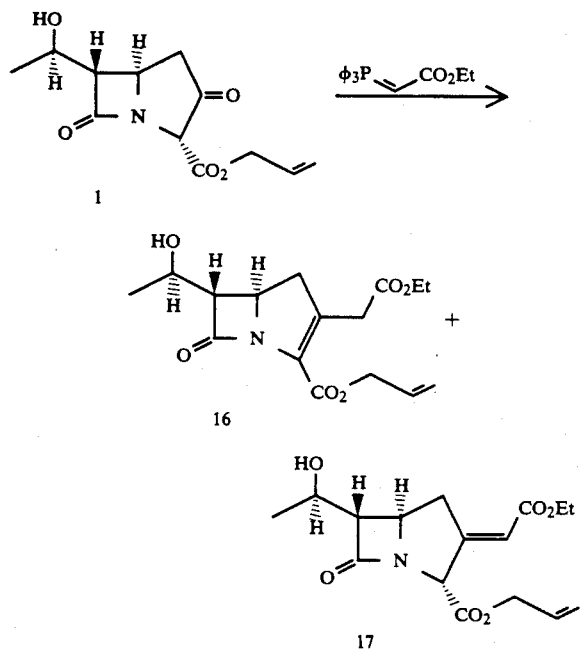

Allyl (5R,6S)-2-carbethoxymethyl-6-[1(R)-hydroxyethyl]carbapen-2-em-3-carboxylate (16) and allyl (5R,6S)-2-[(E)-carbethoxymethylene]-6-[1(R)-hydroxyethyl]carbapenam-3(R)-carboxylate (17)

A solution of the bicyclic ketoester 1 (25.3 mg, 0.1 mmol) and (carbethoxymethylene)triphenylphosphorane (36.6 mg, 0.105 mmol) in anhydrous methylene chloride (1.0 ml) was stirred at room temperature and under a nitrogen atmosphere for 5 hours. The mixture was added to a column of EM silica gel 60 (10 g) that was eluted with 1:1 ethyl acetate-methylene chloride at a rate of 8 ml fractions every 2 minutes. Fraction 5 gave a 1:1 mixture of endo 16 and exo 17 isomers as a clear oil (7 mg), and fractions 6-8 gave a 3:1 mixture of 16 and 17 as a clear oil (17 mg). The total yield of products was 74%.

Compound 16: NMR (CDCl₃) δ 1.27 (t, J=7.2 Hz, CH₃CH₂), b 1.35 (d, J=6.4 Hz, CH₃CH), 3.0 (m, H1aH1b), 3.19 (dd, J=2.9 and 6.7 Hz, H6), 3.60, 3.82 (two d's, J=16.9 Hz, CH₂CO₂), 4.17 (q, J=7.2 Hz, CH₃CH₂), 4.2 (m, H5 and CH₃CH), 4.75 (m, CH₂CH=CH₂), 5.34 (m, CH₂CH=CH₂), 5.95 (m, CH₂CH=CH₂).

Compound 17: NMR (CDCl₃) δ 1.30 (t, J=7.3 Hz, CH₃CH₂), 1.36 (d, J=6.4 Hz, CH₃CH), 2.89 (m, H1a), 3.06 (dd, H6), 3.59 (m, H1b), 4.2 (m, H5, CH₃CH₂, and CH₃CH), 4.66 (m, CH₂CH=CH₂), 5.10 (m, H3), 5.35 (m, CH₂CH=CH₂), 5.95 (m, CH₂CH=CH₂), 6.10 (m, =CHCO₂).

EXAMPLE 9

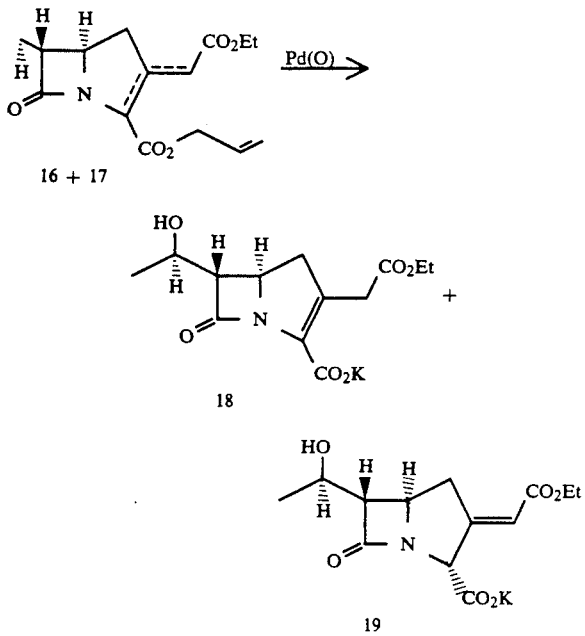

Potassium (5R,6S)-2-carbethoxymethyl-6-[1(R)-hydroxyethyl]carbapen-2-em-3-carboxylate (18) and potassium (5R,6S)-2-[(E)-carbethoxymethylene]-6-[1(R)-hydroxyethyl]carbapenam-3(R)-carboxylate (19)

A 3:1 mixture of isomers 16 and 17 (17.4 mg, 0.054 mmol) and triphenylphosphine (4.2 mg, 0.016 mmol) were dissolved in 1:1 ethyl acetate-methylene chloride (1.0 ml). The solution was treated with 0.5M potassium 2-ethylhexanoate in ethyl acetate (108 μl, 0.054 mmol) and tetrakis(triphenylphosphine)-palladium (5.0 mg, 0.0043 mmol). After stirring 30 minutes at room temperature, the solution was diluted with diethyl ether (5 ml) and the hazy mixture was concentrated under vacuum to an oil. Trituration with ether gave a pale yellow solid. The solid was taken up in water (1 ml), filtered through a Gelman 0.45 μm CR acrodisc, and streaked on two 0.25 mm×20×20 cm Analtech RPS-F plates that were developed in a cold room with 15% ethanol in water. The major UV visible band centered at R_f 0.7 was eluted with 4:1 acetonitrile-water and the eluant diluted with water, washed with petroleum ether, concentrated under vacuum, and lyophilized to give an off-white, amorphous solid. NMR analysis showed a 3:2 mixture of endo 18 and exo 19 Products along with minor amounts of a 3-allylated product similar to 9.

Compound 18: NMR (D₂O) δ 2.94 (m, H1aH1b), 3.38 (dd, J=2.7 and 6.1 Hz, H6), 3.53, 3.79 (two d's, J=16.9 Hz, CH₂CO₂), 4.82 (HOD).

Compound 19: NMR (D₂O)δ3.24 (dd, J=1.7 and 6.3 Hz, H6), 4.82 (HOD), 4.97 (m, H3), 6.17 (m, =CHCO₂).

The NMR solution of 18 and 19 in D₂O was kept at room temperature for 2 days and examined periodically. After 7 hours, there was no change in the 18:19 ratio, no apparent decomposition, and no deuterium exchange. After 48 hours, the ratio of 18:19 was ca. 1:1 and there was no apparent deuterium exchange thereby suggesting some decomposition of the endo product.

EXAMPLE 10

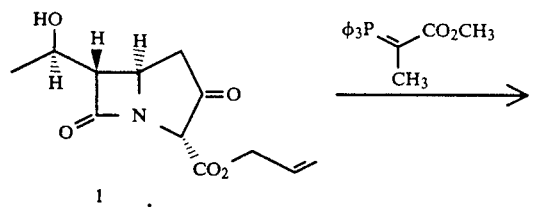

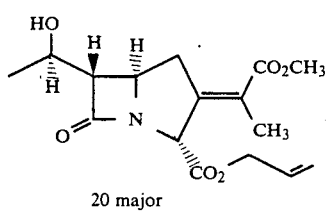

Allyl (5R,6S)-2-[(E)-1-carbomethoxyethylidene]-6-[1(R)-hydroxyethyl]carbapen-3(R)-carboxylate (20)

The bicyclic ketoester 1 (25.3 mg, 0.1 mmol) and (α-carbomethoxyethylidene)triphenylphosphorane (52.3 mg, 0.15 mmol) in chloroform-d (0.5 ml) were kept at room temperature for 3 hours, at 5° C. for 2.5 days, and then at room temperature for an additional 8 hours. The mixture was chromatographed on EM silica gel 60 (5 g) using 1:1 ethyl acetate-methylene chloride as eluting solvent; 8 ml fractions were collected every 1.5 minutes. Fraction 3 gave the exocyclic product 20 (3.9 mg) as an oil and fraction 4 gave a mixture (3.5 mg) containing mainly 20 and some endocyclic product.

Compound 20: NMR (CDCl$_3$) 1.34 (d, J=6.3 Hz, CH$_3$CH), 1.97 (dd, J=1.8 and 2.2 Hz, =CCH$_3$), 3.2 (dd, J=2.2 and 6.6 Hz, H6), 3.3 (m, H1a), 3.36 (qddd, J=2.2, 2.2, 8.1 and 20.1 Hz, H1b), 3.75 (s, CO$_2$CH$_3$), 4.16 (ddd, J=2.2, 5.0 and 8.1 Hz, H5), 4.25 (dq, J=6.4 Hz, CH$_3$CH), 4.63 (m, CH$_2$CH=CH$_2$), 5.21 (br s, H3), 5.30 (m, CH$_2$CH=CH$_2$), 5.88 (m, CH$_2$CH=CH$_2$); IR (CH$_2$Cl$_2$) 3600, 1770, 1745, 1715 cm$^{-1}$; mass spectrum m/e 292 (M$^+$−31), 264, 238, 194, 152.

EXAMPLE 11

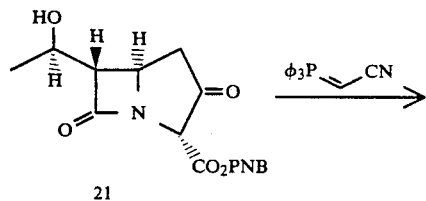

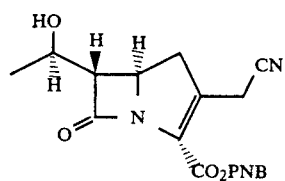

p-Nitrobenzyl (5R,6S)-2-cyanomethyl-6-[1(R)-hydroxyethyl]carbapen-2-em-3-carboxylate (22), p-nitrobenzyl (5R,6S)-2-[(E)-cyanomethylene]-6-[1(R)-hydroxyethyl]-carbapenam-3(R)-carboxylate (23) and p-nitrobenzyl (5R,6S)-2-[(Z)-cyanomethyl]-6-[1(R)-hydroxyethyl]-carbapenam-3(R)-carboxylate (24)

A solution of (cyanomethylene)triphenylphosphorane (30.1 mg, 0.1 mmol) in methylene chloride (0.25 ml) was added to an ice-cold, stirring solution of the bicyclic ketoester 21 (34.8 mg, 0.1 mmol) in methylene chloride (0.75 ml). The resulting solution was stirred under a nitrogen atmosphere at 0° C. for 30 minutes and at room temperature for 5 hours, then stored at −10° C. for 2.5 days, and finally stirred at room temperature for an additional 8 hours. The solution was streaked on an Analtech 0.25 mm×8.5×20 cm silica gel GF plate and the plate was developed with 1:1 methylene chloride-ethylacetate. The major UV visible band was eluted with ethyl acetate and the eluant evaporated under vacuum to give a clear oil (57 mg). NMR examination of this material showed triphenylphosphine oxide and a 4:2:1 mixture of isomeric products 22, 23 and 24. This material was rechromatographed on a 1 mm×20×20 cm silica gel GF plate using 1:1 methylene chloride-ethyl acetate as developing solvent. The major UV visible band centered at R$_f$0.46 gave a similar mixture of products as an oil (43 mg): IR (CH$_2$Cl$_2$) 3590, 1770, 1715, 1525, 1350 cm$^{-1}$.

Compound 22: NMR (CDCl$_3$) δ 1.36 (d,J=6.4 Hz, CH$_3$CH), 3.09 (m, H1aH1b), 3.27 (dd, J=3.1 and 6.8 Hz, H6), 3.74 and 3.96 (two td's, J=1.4 and 18.8 Hz, CH$_2$CN), 4.25 (m, CH$_3$CH), 4.31 (dt, J=3.1 and 8.7 Hz, H5), 5.27 and 5.51 (two d's, J=13.5 Hz, CH$_2$Ar).

Compound 23: NMR (CDCl$_3$) δ 4.16 (dt, J=2.1 and 6.9 Hz, H5), 5.15 (m, H3), 5.63 (m, =CHCN).

Compound 24: NMR (CDCl$_3$) δ 5.39 (m, H3), 5.57 (m, =CHCN).

EXAMPLE 12

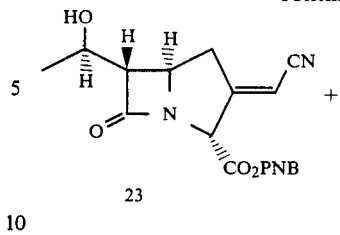

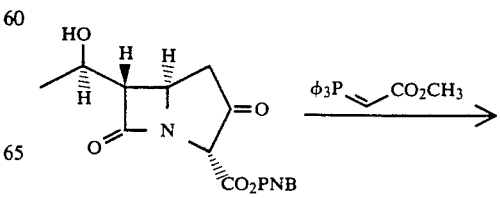

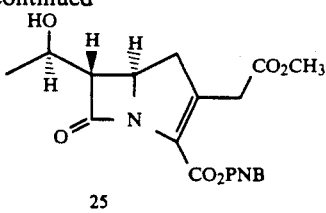

25

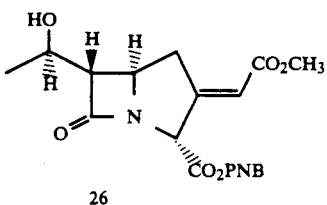

26 p-Nitrobenzyl (5R, 6S)-2-carbomethoxymethyl-6-[1(R)-hydroxyethyl]carbapen-2-em-3-carboxylate (25), and p-nitrobenzyl (5R,6S)-2-[(E)-carbomethoxymethylene]-carbapenam-3(R)-carboxylate (26)

A solution of (carbomethoxymethylene)triphenylphosphorane (35.1 mg, 0.105 mmol) in methylene chloride (0.5 ml) was added dropwise to an ice-cold, stirring solution of bicyclic ketoester 21 (34.8 mg, 0.1 mmol) in methylene chloride (1.0 ml). The resulting solution was stirred at 0° C. under a nitrogen atmosphere for 5 hours, then added to a column of EM silica gel 60 (5 g). The column was eluted with 1:1 methylene chloride-ethyl acetate at a rate of 8 ml factions every 75 seconds. Fractions 6–10 gave a clear oil (28 mg) shown by NMR to be a mixture of triphenylphosphine oxide and a 7:3 ratio of isomeric products 25 and 26.

Compound. 25: NMR (CDCl₃) δ 1.34 (d, J=6.2 Hz, CH₃CH), 2.95 (dd, J=9.2 and 19.2 Hz, H1a), 3.0 J=9.6 and 19.2 Hz, H1b), 3.22 (dd, J=2.9 and 7.0 Hz, H6), 3.62 and 3.83 (two d's, J=16.7 Hz, CH₂CO₂), 3.70 (s, CO₂CH₃), 4.23 (m, CH₃CH), 4.25 (dt, J=2.9 and 9.2 Hz, CH₃CH),5.24 and 5.49 (two d's, J=13.7 Hz, CH₂C₆H₄NO₂).

Compound 26: NMR (CDCl₃) δ 3.73 (s, CO₂CH₃), 5.15 (m, H3), 6.06 (m, =CHCO₂).

EXAMPLE 13

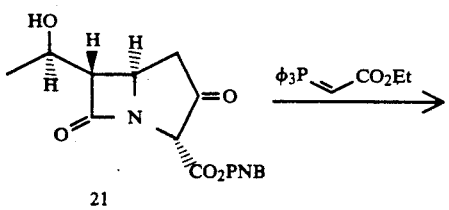

21

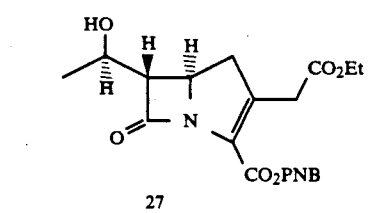

27 p-Nitrobenzyl (5R,6S)-2-carbethoxymethyl-6-[1(R)-hydroxyethyl]carbapen-2-em-3-carboxylate (27)

A solution of bicyclic ketoester 21 (34.8 mg, 0.1 mmol) in anhydrous methylene chloride (1.0 ml) was cooled in an ice-bath under a nitrogen atmosphere and treated dropwise with a solution of (carbethoxymethylene)triphenylphosphorane (34.8 mg, 0.1 mmol) in anhydrous methylene chloride (0.5 ml). The resulting solution was stirred at 0° C. for 6 hours, then added to a column of EM silica gel 60 (5 g). The column was eluted with 1:1 ethylacetatemethylene chloride at a rate of 8 ml fractors per minute. Fractions 3–5 gave the product as an oil (22 mg, 53%) which solidified on trituration with diethyl ether to afford 27 as small, white fibers, m.p. 102°–104° C.: NMR (CDCl₃) δ 1.26 (t, J=7.1 Hz, CH₂CH₃), 1.36 (d, J=6.2 Hz, CH₃CH), 1.86 (d, J=4.8 Hz, OH), 2.96 (dd, J=9.0 and 19.0 Hz, H1a), 3.08 (dd, J=9.6 and 19.0 Hz, H1b), 3.22 (dd, J=3.0 and 6.6 Hz, H6), 3.61 and 3.83 (two d's, J=16.6 Hz, CH₂CO₂), 4.16 (q, J=7.1 Hz, CH₂CH₃), 4.24 (m, H5 and CH₃CH), 5.25 and 5.49 two d's, J=13.8 Hz, CH₂C₆H₄NO₂), 7.66 and 8.24 (two d's, J=8.7 Hz, C₆H₄NO₂); IR (CH₂Cl₂) 3590, 1775, 1725 (br), 1520, 1350 cm⁻¹; UV (dioxane) λ$_{max}$ 273 nm (ε 14,300); mass spectrum m/e 418 (M⁺), 400, 373, 345, 333, 332, 287, 259, 136.

EXAMPLE 14

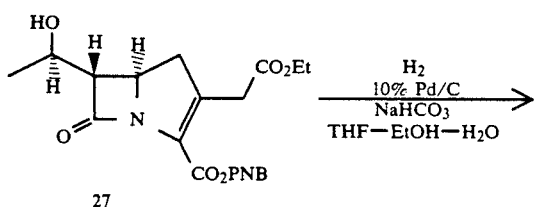

27

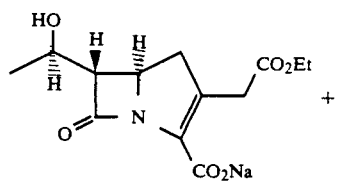

28 trace

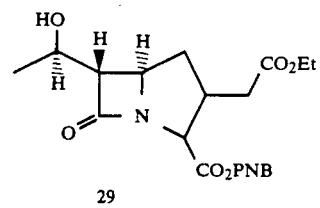

29

Sodium (5R,6S)-2-carbethoxymethyl-6-[1(R)-hydroxymethyl]-carbapen-2-em-3-carboxylate (28) and sodium (5R,6S)-2(R,S)-carbethoxymethyl-6-[1(R)-hydroxyethyl]-carbapenam-3(R,S)-carboxylate (29)

A solution of diester 27 (5.2 mg, 0.0125 mmol) in tetrahydrofuran (0.9 ml) was diluted with ethanol (0.9 ml) and deionized water (0.7 ml) containing sodium carbonate (1.05 mg, 0.0125 mmol). The resulting solution was mixed with 10% palladium on charcoal (5 mg) and stirred under a hydrogen atmosphere at room temperature. Aliquots (20 μl) were periodically removed, added to dioxane (1.5 ml) and examined by UV, which showed rapid loss of the starting material chromophore at 273 nm over 60 minutes. The reaction mixture was diluted with water (5 ml) and filtered through a Celite pad, and the filtrate was washed with diethylether (3×5 ml). UV analysis of the resulting aqueous phase (7.3 ml) showed the presence of 3.8 hydroxyamine extinguished optical density units at $\lambda_{max}$ 270 nm, which corresponds to a 6% yield of 28 by assuming $\epsilon$ext. 5000. The aqueous solution was concentrated under vacuum to ca. 1 ml and lyophilized to provide n amorphous, white solid. The IR and NMR spectra of this material were consistent with a mixture of isomeric carbapenams 29: IR (Nujol) 1760 (sh), 1730, 1610 cm$^{-1}$; NMR (D$_2$O) $\delta$ 1.28 (m and CH$_3$CH$_2$), 1.55–2.28 (m, HlaHlb), 2.55 (m, CH$_2$CO$_2$), 3.15 (m, H2), 3.21 (dd, H6), 3.80 (m, H5), 3.88 (d, H3), 4.19 (m, CH$_3$CH and CH$_3$CH$_2$).

EXAMPLE 15

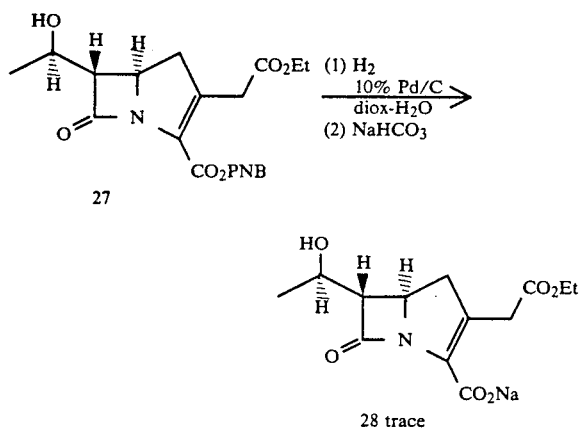

27

28 trace

Sodium (5R,6S)-2-carbethoxymethyl-6-[1(R)-hydroxymethyl]-carbapen-2-em-3-carboxylate (28)

A solution of diester 27 (5.2 mg, 0.0125 mmol) in 7:3 dioxane-water (1.0 ml) was added to a prereduced mixture of 10% palladium on charcoal (5 mg) in 7:3 dioxane-water, and the resulting mixture was stirred under a hydrogen atmosphere at room temperature. Aliquots (20 μl) were removed periodically, added to dioxane (1.5 ml) and examined by UV. The starting material chromophore at 273 nm rapidly disappeared followed by a slower decrease in absorption near 285 nm. After 90 minutes, the reaction mixture was diluted with water (1 ml) containing sodium bicarbonate (1.05 mg, 0.0125 mmol) and stirred a few minutes. The mixture was filtered through a Celite Pad and the catalyst washed with water (5 ml). The filtrate was washed with diethylether (3×5 ml) UV analysis of the aqueous solution (6.8 ml) showed the presence of 6.8 hydroxyamine extinguished optical density units at 270 nm, which corresponds to 0.4 mg (11%) of compound 28 by assuming $\epsilon$ext. 5000 for 28 at $\lambda_{max}$ 270 nm.

EXAMPLE 16

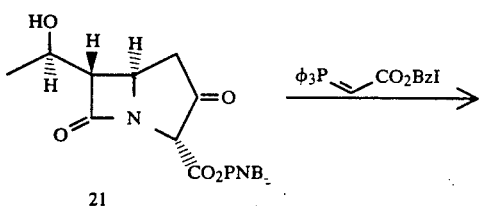

21

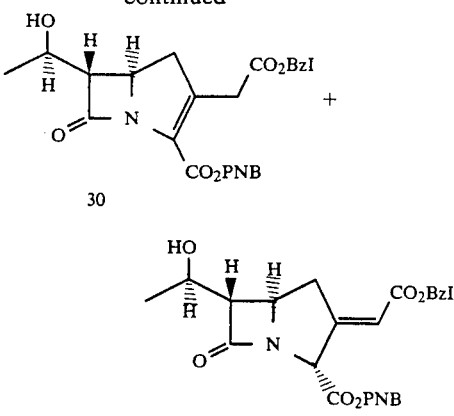

30

31 p-Nitrobenzyl (5R,6S)-2-carbobenzyloxymethyl-6-[1(R)-hydroxyethyl]carbapen-2-em-3-carboxylate (30) and p-nitrobenzyl (5R,6S)-2-[(E)-carbobenzyloxymethylene-6-[1(R)-hydroxyethyl]carbapen-2-em-3-carboxylate (31)

A solution of (carbobenzyloxymethyl)triphenylphosphorane (43.1 mg, 0.105 mmol) in methylene chloride (0.5 ml) was added dropwise to an ice-cold, stirring solution of the bicyclic ketoester 21 (34.8 mg, 0.1 mmol). The resulting solution was stirred in the cold and under a nitrogen atmosphere for 4 hours. The solution was added to a column of EM silica gel 60 (5 g) that was eluted with 2:1 methylene chloride-ethylacetate at a rate of 5 ml fractions every 100 seconds. Fractions 5–10 gave the bicyclic product (9.1 mg, 19%) as a gum. NMR examination of this material showed a 5:1 ratio of endo and exo products 30 and 31.

Repetition of the procedure on a 10-fold scale up gave the bicyclic product (43 mg) as an oil. Trituration of this material with diethyl ether gave endo isomer 30 (33 mg) as white crystals, m.p. 98°–100°: NMR (CDCl$_3$) $\delta$ 1.35 (d, J=6.4 Hz, CH$_3$CH), 1.87 (d, J=4.6 Hz, OH), 2.93 (dd, J=9.0 and 19.0 Hz, Hla), 3.05 (dd, J=9.6 and 19.0 Hz, Hlb), 3.19 (dd, J=2.9 and 6.5 Hz, H6), 3.69 and 3.88 (two d's, J=16.8 Hz, CH$_2$CO$_2$), 4.23 (dt, J=2.9 and 9.3 Hz, H5), 4.26 (m CH$_3$CH), 5.15 (s, CH$_2$C$_6$H$_5$), 5.23 and 5.47 (two d's, J=14.0 Hz, CH$_2$C$_6$H$_4$NO$_2$), 7.38 (m, C$_6$H$_5$), 7.64 and 8.22 (two d's, J=9.0 Hz, C$_6$H$_4$NO$_2$); IR (CH$_2$Cl$_2$) 3590, 1770, 1727, 1715 (sh), 1540, 1345 cm$^{-1}$; UV (dioxan) $\lambda_{max}$ 273 nm ($\epsilon$14,600); mass spectrum m/e 480 (M$^+$), 462, 436, 394, 345, 300, 259.

The exocyclic isomer 31 had characteristic NMR (CDCl$_3$) resonances at 6 5.20 (s, CH$_2$C$_6$H$_5$) and 6.13 (m, =CHCO$_2$).

EXAMPLE 17

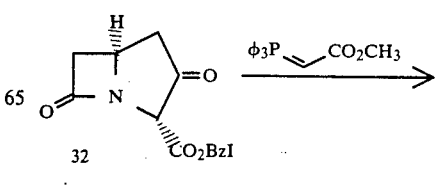

32

TABLE I
Relative Antibacterial Activities of Selected Analogs

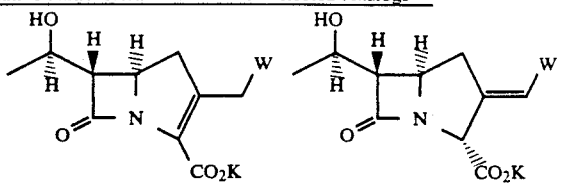

| W | | CO₂Me | CO₂Bzl | CN | CO₂Me | CN |
|---|---|---|---|---|---|---|
| S. aureus | (4) | 1.4 | 2.8 | 0.4 | 0.1 | 0.5 |
| Enterococcus | (3) | 1.7 | 3.5 | 0.9 | 0.1 | 0.3 |
| E. coli | (5) | 4.9 | 0.2 | 2.0 | 0.7 | 0.8 |
| Enterbactor | (6) | 13.0 | 0.2 | 2.5 | 0.4 | 1.0 |
| Klebsiella | (5) | 6.1 | 0.1 | 1.5 | 0.2 | 0.4 |
| Serratia | (2) | 32.0 | 0.2 | 3.7 | 0.7 | 0.4 |
| Proteus | (5) | 6.1 | 3.7 | 2.6 | 0.1 | 0.4 |
| Ps. aeruginosa | (5) | 1.7 | 3.2 | 3.7 | 0.01 | 0.03 |

Agar disc-diffusion assay. Activities are relative to thienamycin = 1 and are expressed as indices derived from the indicated number of strains in each species.

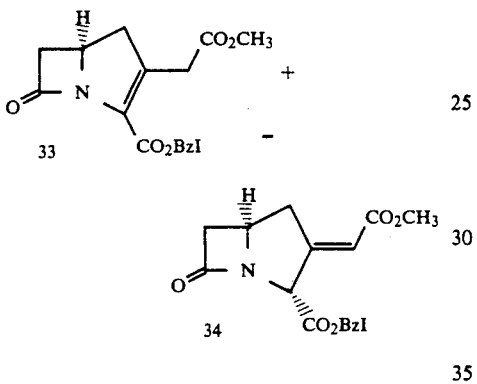

Benzyl (5R)-2-(carbomethoxymethyl)carbapen-2-em-3-carboxylate (33) and benzyl (5R)-2-[(E)-carbomethoxymethylene]carbapenam-3(R)-carboxylate (34)*

A solution of bicyclic ketoester 32 (25.9 mg, 0.1 mmol) and (carbomethoxy)triphenylphosphorane

*The compounds of this example are racemic, but are shown as one enantiomer for clarity. (35.1 mg, 0.105 mmol) in chloroform-d (0.5 ml) was kept at room temperature under a nitrogen atmosphere. After 65 minutes, the solution was added to a column of EM silica gel 60 (5 g) which was eluted with 1:1 ethylacetate-methyldene chloride at a rate of 8 ml fractions/minute. Fraction 2 gave a clear oil (21.4 mg, 68%) shown by NMR to be a 3:2 mixture of products 33 and 34: IR (film) 1775, 1735, 1715 cm$^{-1}$; mass spectrum m/e 315 (M$^+$), 287, 273, 224.

Compound 33: NMR (CDCl$_3$) δ 2.90 and 3.02 (ABX, J=18.1, 8.7 and 9.8 Hz, H1aH1b), 2.96 (dd, J=3.0 and 16.5 Hz, H6α), 3.47 (dd, J=5.5 and 16.5 Hz, H6β), 3.60 and 3.85 (ABq, J=16.8 Hz, CH$_2$CO$_2$), 3.69 (s, CO$_2$CH$_3$), 4.22 (dddd, J=3.0, 5.5, 8.7, 9.8 Hz, H5), 5.24 and 5.33 (ABq, J=12.5 Hz, CH$_2$C$_6$H$_5$), 7.4 (m, C$_6$H$_5$).

Compound 34: NMR (CDCl$_3$) δ 2.79 (m, H1a), 2.81 (dd, J=2.1 and 16.2 Hz, H6β), 3.49 (dd, J=5.0 and 16.2 Hz, H6α), 3.62 (m, H1b), 3.74 (s, CO$_2$CH$_3$), 4.13 (m, H5), 5.12 (m, H3), 5.20 (s, CH$_2$C$_6$H$_5$), 6.09 (m, =CHCO$_2$), 7.4 (m, C$_6$H$_5$).

EXAMPLE 18

The antibacterial activity of compounds 4, 5, 10, 11, and 14 were determined by a disc-diffusion assay employing the Kirby-Bauer method (A. W. Bauer, W. M. Kirby, J. C. Sherris, and M. Turk, Am. J. Clin. Pathol., 1966, 45, 493), modified only by the use of an agar thickness of 0.2 cm. The activities are reported below in Table I. The activities are relative to thienamycin=1 and are expressed as indexes derived from the indicated number of strains in each species.

What is claimed is:

1. A compound of the structural formula:

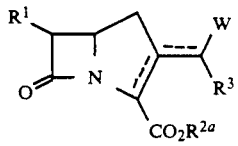

wherein R$^1$ is independently selected from C$_1$–C$_3$ linear or branched alkyl substituted with hydroxy or protected hydroxy; R$^{2a}$ is an ester protecting group, H, or a water-soluble cation; R$^3$ is H or C$_1$–C$_4$ alkyl; W is CN wherein the dotted line represents an endo or exo double bond, or mixture thereof.

2. The compound of claim 1 of the structural formula:

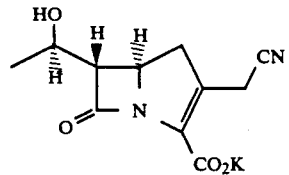

3. The compound of claim 1 of the structural formula:

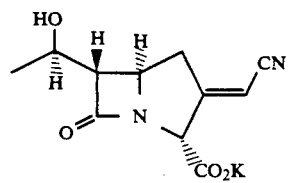

4. A compound of the structural formula:

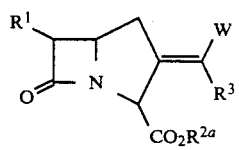

wherein $R^1$ is independently selected from $C_1$-$C_3$ linear or branched alkyl substituted with hydroxy or protected hydroxy; $R^{2a}$ is an ester protecting group, H, or a water-soluble cation; $R^3$ is H or $C_1$-$C_4$ alkyl; W is $CO_2R^4$ wherein $R^4$ is selected from $C_1$-$C_4$ alkyl or $C_7$-$C_{11}$ aralkyl; wherein the aryl portion is phenyl, or phenyl substituted with chloro $C_1$-$C_3$ alkoxy or di ($C_1$-$C_3$ alkyl) amino.

5. The compound of claim 4 of the structural formula:

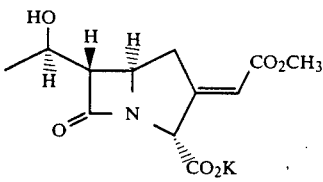

6. The compound of claim 4 of the structural formula:

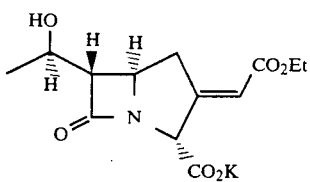

wherein Et is ethyl.

7. The compound of claim 4 of the structural formula:

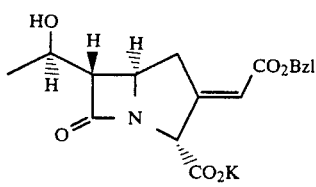

wherein Bzl is benzyl.

8. The compound of claim 4 of the structural formula:

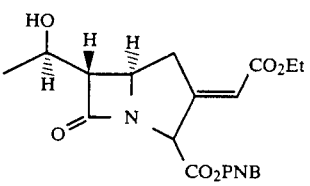

where PNB is p-nitrobenzyl.

9. The compound of claim 4 of the structural formula:

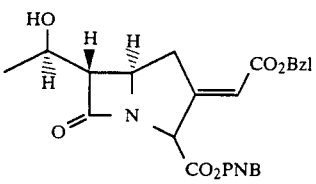

* * * * *